United States Patent [19]

Harada et al.

[11] Patent Number: 5,744,604
[45] Date of Patent: Apr. 28, 1998

[54] PREPARATION OF 3-OXY-5-OXO-6-HEPTENOIC ACID DERIVATIVES

[75] Inventors: Katsumasa Harada; Akio Matsushita; Yasuhiro Kawachi; Hiroshi Sasaki, all of Yamaguchi, Japan

[73] Assignee: Ube Industries, Ltd., Yamaguchi, Japan

[21] Appl. No.: 858,937

[22] Filed: May 20, 1997

Related U.S. Application Data

[63] Continuation of Ser. No. 524,045, Sep. 6, 1995, Pat. No. 5,677,455.

[30] Foreign Application Priority Data

Sep. 6, 1994 [JP] Japan ................................. 6-212959
Sep. 6, 1994 [JP] Japan ................................. 6-212961

[51] Int. Cl.$^6$ .......................................................... C07F 7/02
[52] U.S. Cl. ............................................................. 546/14
[58] Field of Search ................................................. 546/14

[56] References Cited

FOREIGN PATENT DOCUMENTS

93/02089  2/1993  WIPO.

OTHER PUBLICATIONS

Blackwell, C.M., et al, *J. Org. Chem.*, 57:1935–1937 (1992).

*Primary Examiner*—Amelia Owens
*Attorney, Agent, or Firm*—McAulay Fisher Nissen Goldberg & Kiel, LLP

[57] ABSTRACT

Methyl (3R, 6E)-3-[(tert-butyldimethylsilyl)oxy]-7-[2', 6'-diisopropyl-4'-(4"-fluorophenyl)-5'-(methoxymethyl) pyridin-3'-yl]-5-oxy-6-heptenoate or other 3-oxy-5-oxo-6-heptenoic acid derivative is prepared by the reaction of an aromatic aldehyde and an oxyglutaric acid derivative in an aliphatic alcohol containing a small amount of water in the presence of an alkali metal carbonate or hydrogen carbonate.

4 Claims, No Drawings

PREPARATION OF 3-OXY-5-OXO-6-HEPTENOIC ACID DERIVATIVES

This is a continuation of application Ser. No. 08/524,045 filed Sep. 6, 1995 now U.S. Pat. No. 5,677,455.

FIELD OF THE INVENTION

The present invention relates to a process for preparing 3-oxy-5-oxo-6-heptenoic acid derivatives which are of value as intermediates for the preparation of a blood cholesterol reducing agent.

BACKGROUND OF THE INVENTION

It is known that HMG-Co A (i.e., 3-hydroxy-3-methylglutaryl Coenzyme-A) reductase preventive agents are effective as blood cholesterol reducing agents. Representative examples of the HMG-Co A reductase preventive agents having blood cholesterol reducing activity include (+)-trans-(E)-6-[2-(2,4-dichlorophenyl)ethenyl]-3,4,5,6-tetrahydroxy-2H-pyran-2-one and sodium (3R,5S,6E) -(+)-erythro-7-[2',6'-diisopropyl-4'-(4"-fluorophenyl)-5'-(methoxymethyl)pyridin-3'-yl]-3,5-dihydroxy-6-heptenoate.

The former "pyran-2-one" compound is prepared from methyl (3R, 6E)-3[(tert-butyldimethylsilyl)oxy]l-7-(2,4-dichlorophenyl)-5-oxo-6-heptenoate (which is one of 3-oxy-5-oxo-6-heptenoate derivatives) via the following route:

The methyl (3R,6E)-3[(tert-butyldimethylsilyl)oxy]-7-(2,4-dichlorophenyl)-5-oxo-6-heptenoate is treated with hydrogen fluoride to remove the tert-butyldimethylsilyl group so as to give methyl (3R,6E)-7-(2,4-dichlorophenyl)-5-oxo-3-hydroxy-6-heptenoate, which is in turn converted into methyl (3R,5S,6E)-7-(2,4-dichlorophenyl)-3,5-dihydroxy-6-heptenoate by the Syn reduction using diethylmethoxyborane and sodium borohydride, in the manner described in Japanese Patent Provisional Publication H5(1993)-178841. Thus obtained methyl (3R,5S, 6E)-7-(2, 4-dichlorophenyl)-3,5-dihydroxy-6-heptenoate is treated with sodium hydroxide and hydrochloric acid in the manner as described in Journal of Medicinal Chemistry, 1985, vol.28, No.3, pp. 347–358, to give the (+)-trans-(E)-6-[2-(2,4-dichlorophenyl)ethenyl]-3,4,5,6-tetrahydroxy-2H-pyran-2-one having the HMG-Co A reductase preventive action.

Heretofore, the 3-oxy-5-oxo-6-heptenoate derivative is prepared by one of the following three processes:

(1) An aromatic aldehyde (benzaldehyde) and an oxyglutaric acid ester {methyl (R)-3-[(tert-butyldimethylsilyl)oxy]-6-dimethoxyphosphinyl)-5-oxyhexanoate} are caused to react in an acetonitrile solvent in the presence of lithium chloride using 1,8-diazabicyclo-[5,4,0]-undecan-7-ene (hereinafter referred to as DBU) as a base to give methyl (3R,6E)-3-[(tert-butyldimethylsilyl)oxy]-5-oxo-7-phenyl-6-heptenoate, which is described in Bioorganic & Medicinal Chemistry Letters, 1991, vol. 1, No. 3, pp.161–164. This process appears disadvantageous for industrial use because the yield is so low as 71% and an expensive DBU is necessarily employed as the base.

(2) A heterocyclic aromatic aldehyde [6-fluoro-4-(4-fluorophenyl)-2-(1-methylethyl)-3-quinolinecarbaldehyde] and an oxyglutaric acid ester {(3R,1',S}-1-(1'-naphthyl)ethyl-3-[(tert-butyldimethylsilyl)oxy]-6-(dimethoxyphosphinyl)-5-oxo-hexanoate} are caused to react in a dichloromethane solvent in the presence of lithium chloride using DBU to give [R-(R*,R*)]-1-phenylethyl-3-[(tert-butyldimethylsilyl)oxy]-7-[6-fluoro-4-(4-fluorophenyl)-2-(1-methylethyl)-3-quinolyl]-5-oxo--6-heptenoate, which is described in Journal of Medicinal Chemistry, 1991, vol.34, No.1, pp.367–373. This process also appears unsatisfactory for industrial use because of low yield such as 33%.

(3) An aliphatic aldehyde {(1S,2S,4aR,4S,8S,8aS)-1,2,4a,5,6,7,8,8a-octahydro-2-methyl-8-[(2",2"-dimethyl-1"-oxo-butyl)oxy]-6-[(E)-prop-1-enyl]naphthalene-1-carbaldehyde} and an oxyglutaric acid ester derivative {methyl (R)-3-[(tert-butyldimethylsilyl)oxy]-6-(dimethoxyphosphinyl)-5-oxohexanoate} are caused to react in an isopropanol solvent using potassium carbonate or cesium carbonate as a base to give methyl (1S,2S,4aR,6S,8S,8aS,3'R)-7'-[1,2,4a,5,6,7,8,8a-octahydro-2-methyl-8-[(2",2"-dimethyl-1"-oxo-butyl)oxy]-6-[(E)-prop-1-enyl]naphthalenyl]-3'-[(tert-butyldimethylsilyl)oxy]-5'-oxo-6'-heptenoate, which is described in Journal of Organic Chemistry, 1992, vol. 57, No.6, pp.1935–1937. This process also appears unsatisfactory for industrial use because the reaction rate is very low to the extent that 2 to 3 days are necessary to complete the reaction, and further the conversion ratio is as low as 25%, and the yield also is low. This publication further teaches the same reaction in a tert-butanol solvent using cesium carbonate as a base. This process is also disadvantageous for industrial use because the reaction rate is low such that the conversion ratio of the starting material is 78% after the reaction of four days and the yield is as low as 53%.

(4) Recently, Japanese Patent Provisional Publication H6(1994)-107673 proposes a process for preparing a 3-oxy-5-oxo-6-heptenoic acid derivative of the formula:

wherein Ar is a quinolyl group which may haves substituents, $R^1$ is an alkyl group and the like, and $R^2$ is a hydrogen or a hydroxyl-protective group, which comprises reacting a quinolyl aldehyde with an oxyglutaryl acid derivative having the formula:

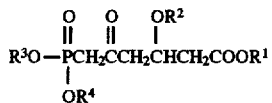

wherein $R^1$ and $R^2$ have the same meanings as above, and each of $R^3$ and $R^4$ independently is a hydrogen atom, an alkyl group, and the like, in a dry organic solvent, in the presence of a base. This process still appears unsatisfactory because the yield is as low as approximately 60%.

Another example of the 3-hydroxy-3-methylglutaryl Coenzyme A reductase preventive agents having blood cholesterol reducing activity, namely, sodium (3R,5S,6E)-(+)-erythro-7-[2',6'-diisopropyl-4'-(4"-fluorophenyl)-5'-(methoxymethyl)pyridin-3'-yl]-3,5-dihydroxy-(6-heptenoate can be prepared in the combination of the synthesis process described in Japanese Patent Provisional Publication H1(1989)-216974 and the optical resolution process described in Japanese Patent Provisional Publication H4(1992)-308573.

The former synthesis process comprises the following two steps:

Step (1): (E)-3-[2',6'-diisopropyl-4'-(4"-fluorophenyl)-5'-(methoxymethyl)pyrid-3'-yl]prop-2-enal and methyl acetoacetate are caused to react to give methyl (E)-7-[2',6'-diisopropyl-4'-(4"-fluorophenyl)-5'-(methoxymethyl)pyrid-3'-yl]-5-hydroxy-3-oxohept-6-enoate (hereinafter referred to as 1 Hydroxyl compound); and Step (2): The above-obtained 1 Hydroxyl compound is reduced by Syn Reduction using triethylborane and sodium borohydride to methyl erythro-(E)-7-[2',6'-diisopropyl-4'-(4to-fluorophenyl)-5'-(methoxymethyl)pyrid-3'-yl]-3,5-dihydroxyhept-6-enoate (racemate, hereinafter referred to as 2 Hydroxyl compound).

The latter optical resolution process comprises the following two steps:

Step (3): The racemate of 2-Hydroxyl compound obtained in Step (2) is caused to react with R-(+)-phenetylamine to yield two diastereomers of (1'''R)-N-(1'''-phenylethyl)-erythro-(E)-7-[2',6'-diisopropyl-4'-(4"-fluorophenyl)-5'-methoxymethyl)pyrid-3'-yl]-3,5-dihydroxyhept-6-enamide; and Step (4): The diastereomer obtained in Step (3) is optically resolved by column chromatography to give (6E,3R,5S,1'''R)-N-(1'''-phenylethyl)-(+)-erythro-7-[2',6'-diisopropyl-4'-(4"-fluorophenyl)-5'-(methoxymethyl)pyrid-3'-yl]-3,5-dihydroxyhept-6-enamide (hereinafter referred to as Optically active amide).

Finally, the Optically active amide obtained in Step (4) is treated with hydrochloric acid and sodium hydroxide to obtain the desired product.

According to the above-described process;, the 1 Hydroxyl compound is obtained as a racemate because the starting compound is an acetoacetic acid ester having no asymmetric carbon atom, and hence the 2 Hydroxyl compound derived from the 1 Hydroxyl compound is obtained as a racemate. The 2 Hydroxyl compound is required to be optically resolved to obtain an optically active desired compound. As a result, unnecessary products are also obtained. The by-products (which have different optical configurations) derived from the racemate of 2 Hydroxyl compound are resistant to selective racemization because the racemate of 2 Hydroxyl compound has two asymmetric carbon atoms (therefore, there are four different optical isomers). Accordingly, it is very difficult to convert the by-products to the desired racemate for effectively use of the by-products. This is disadvantageous from the viewpoint of industrial use.

SUMMARY OF THE INVENTION

Accordingly, the object of the present invention is to provide a new process for preparing the :3-oxy-5-oxo-6-heptenoic acid derivatives which shows a high yield and is advantageously employable for industrial use.

The present invention provides a process for the preparation of a 3-oxy-5-oxo-6-heptenoic acid derivative having the formula:

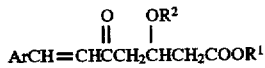

wherein Ar is an aromatic group, $R^1$ is an aliphatic group, and $R^2$ is a hydroxyl-protective group, which comprises reacting an aromatic aldehyde having the formula:

wherein Ar has the same meaning as above, with an oxyglutaric acid derivative having the formula:

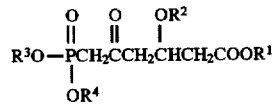

wherein $R^1$ and $R^2$ have the same meanings as above, and each of $R^3$ and $R^4$ independently is a hydrocarbon group, in a solvent of an aliphatic alcohol containing 30 to 20,000 ppm of water, in the presence of a base having the formula:

$$M_xA$$

wherein M is an alkali metal, A is a carbonic or hydrogen carbonic group, and x is 1 or 2.

The present invention is made on the following finding by the inventors: that is, the known process comprising the reaction of the aromatic aldehyde and the oxyglutaric acid derivative in an organic solvent in the presence of a base is surprisingly improved in its reaction rate and the yield of the desired product by employing as the solvent an aliphatic alcohol containing a small amount of water.

The invention further provides methyl (3R,6E)-3-(tert-butyldimethylsilyl)oxy]-7-[2',6'-diisopropyl-4'-(4"-fluorophenyl)-5-(methoxymethyl)pyridin-3-yl)-5-oxo-6-heptenoate, which is a new compound and is advantageously employable for preparing sodium (3R,5S,6E)-(+)-erythro-7-[2', 6'-diisopropyl-4'-(4"-fluorophenyl)-5'-(methoxymethyl) pyridin-3'-yl]-3,5-dihydroxy-6-heptenoate which is known as the 3-hydroxy-3-methylglutaryl Coenzyme A reductase preventive agent having blood cholesterol reducing activity.

The above-identified methyl (3R,6E)-3-[(tert-butyldimethylsilyl)oxy]-7-[2', 6'-diisopropyl-4'-(4"-fluorophenyl)-5'-(methoxymethyl)pyridin-3'-yl]-5-oxo-6-heptenoate is represented by the following formula:

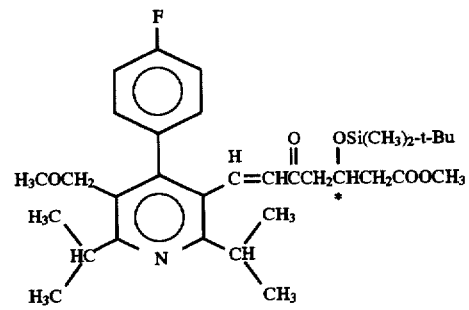

DETAILED DESCRIPTION OF THE INVENTION

The 3-oxy-5-oxo-6-heptenoic acid derivative prepared by the process of the invention has the following formula (1):

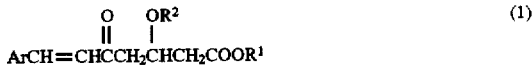

(1)

wherein Ar is an aromatic group, $R^1$ is an aliphatic group, and $R^2$ is a hydroxyl-protective group.

The aromatic group for Ar is either a hydrocarbonic aromatic group (i.e., non-heterocyclic aromatic group) or a heterocyclic aromatic group of a single ring type or a condensed ring type. These aromatic groups may have one or more substituents.

Examples of the hydrocarbonic aromatic groups include an aryl group such as phenyl or naphthyl. Examples of the heterocyclic aromatic groups include pyridyl, quinolyl, pyrolyl, indolyl, pyrimidyl, pyrazolyl, pyridazyl, imidazolyl, furyl, and thienyl.

Examples of the substituents include an alkyl group having 1–10 carbon atoms (e.g., methyl, ethyl, propyl, butyl, pentyl, or hexyl), an alkenyl group (e.g., vinyl, allyl, or isopropenyl), an alkynyl group (e.g., ethynyl or 2-propynyl), a cycloalkyl group (e.g., cyclopropyl, cyclopentyl, or cyclohexyl), an aryl group (e.g., phenyl, or naphthyl), a substituted lower alkyl group having 1–6 carbon atoms (e.g., methoxymethyl, ethoxymethyl, hydroxymethyl, aminomethyl, dimethylaminomethyl, benzyl, trityl, or naphthylmethyl), a substituted aryl group (e.g., 4-fluorophenyl, tolyl, mesityl, or 4-methoxyphenyl), a halogen atom (e.g., fluorine, chlorine, or bromine), an amino group, a substituted amino group (e.g., methylamino, dimethylamino, or anilino), a phenoxy group, a carboxyl group, an alkoxycarbonyl group (e.g., methoxycarbonyl or ethoxycarbonyl), an aryloxycarbonyl group (e.g., phenoxycarbonyl or naphthyloxycarbonyl), an acyl group (e.g., acetyl or benzoyl), an acyloxy group (e.g., acetyloxy, benzoyloxy, or 2,2-dimethylbutyloyloxy), an aromatic heterocyclic group (e.g., indolyl, pyridyl, pyrimidyl, quinolyl, pyrazolyl, pyridazyl, imidazolyl, pyrolyl, furyl, or thienyl), and a saturated heterocyclic group (e.g., morpholino, piperidino, or pyridinyl).

Preferred aromatic group for Ar include a phenyl group; a substituted phenyl group such as 4-tolyl, 4-chlorophenyl, 2,4-dichlorophenyl, 4-methoxyphenyl, 3,5-dichloro-6-(4-fluorophenyl)phenyl or 2,4-dimethyl-6-(4-fluoro-3-methylphenyl)phenyl; a pyridyl group; a substituted pyridyl group such as 4-phenyl-2-methylpyridin-3-yl, 2-isopropyl-6-phenyl-4-(4-fluorophenyl)-5-methoxymethylpyridin-3-yl, 2,5-diisopropyl-4-(4-fluorophenyl)-pyridin-3-yl, 2,6-diisopropyl-4-(4-fluorophenyl)-5-methoxymethyl-3-yl, or 2,6-diisopropyl-4-(4-fluorophenyl)pyridin-3-yl; a quinolyl group; a substituted quinolyl group such as 2-(4-fluorophenyl)-4-isopropylquinolin-3-yl; a pyrimidyl group; a substituted pyrimidyl group such as 6-isopropyl-2-phenyl-4-(4-fluorophenyl)pyrimidin-5-yl, 6-methyl-2-phenyl-4-(4-fluorophenyl)pyrimidin-5-yl, 2,4-dimethyl-6-(4-fluorophenyl)pyrimidin-5-yl, or 2-(N-methyl-N-methanesulfonyl)amino-4-isopropyl-6-(4-fluorophenyl) pyrimidin-5-yl; a pyrolyl group; a substituted pyrolyl group such as 2-isopropyl-1-phenyl-4-(4-fluorophenyl)-pyrol-3-yl; an indolyl group; a substituted indolyl group such as 3-(4-fluorophenyl)-1-isopropylindol-2-yl; a pyrazolyl group; a substituted pyrazolyl group such as 5-(4-fluorophenyl)-3-isopropyl -1-phenylpyrazol-4-yl; a pyridazyl group; a substituted pyridazyl group such as 3,4-bis(4-fluorophenyl)-6-isopropylpiridazin-5-yl; an imidazolyl group; and a substituted imidazolyl group such as 4-isopropyl-2-phenyl-1-(4-fluorophenyl)-1H-imidazol-5-yl.

The aliphatic group for $R^1$ is a straight-chain or branched-chain alkyl group having 1–16 carbon atoms, preferably 1–8 carbon atoms, most preferably 1–6 carbon atoms. The alkyl group may have one or more substituents. Examples of the alkyl groups include methyl, ethyl, propyl, isopropyl, butyl, isobutyl, tert-butyl, pentyl, its isomers, hexyl, its isomers, heptyl, its isomers, octyl, its isomers, nonyl, its isomers, decyl, and its isomers. Preferred are methyl, ethyl, propyl, isopropyl, butyl, isobutyl, and tert-butyl. Most preferred are methyl and ethyl. Examples of the substituents include aryl groups such as phenyl and naphthyl. Therefore, examples of the substituted alkyl groups have 7–14 carbon atoms and include phenylmethyl (i.e., benzyl), naphthylmethyl, phenylethyl, and naphthylethyl. Preferred are phenylethyl and naphthylethyl.

Examples of the hydroxyl-protective group for $R^2$ include ether-forming protective groups such as methyl, ethyl, propyl, butyl, tert-butyl, allyl, benzyl, tetrahydropyranyl, tert-butyldimethylsilyl, and tert-butyldiphenylsilyl, and an ester-forming protective groups such as acetyl and benzoyl. Preferred is tert-butyldimethylsilyl.

According to the present invention, the 3-oxy-5-oxo-6-heptenoic acid derivative of the formula (1) is prepared by the reaction of an aromatic aldehyde having the formula (2):

wherein Ar has the same meaning as above, and an oxyglutaric acid derivative having the formula (3):

wherein $R^1$ and $R^2$ have the same meanings as described above, and each of $R^3$ and $R^4$ independently is a hydrocarbon group.

Examples of the hydrocarbon groups for $R^3$ and $R^4$ include an alkyl group having 1–5 carbon atoms, an aralkyl group having alkyl of 1–5 carbon atoms, a halogeno aralkyl group having alkyl of 1–5 carbon atoms, and an aryl group such as phenyl.

Examples of the alkyl groups having 1–5 carbon atoms include methyl, ethyl, propyl, isopropyl, butyl, isobutyl, tert-butyl, pentyl, and its isomers. Examples of the aralkyl groups have 7–9 carbon atoms and include benzyl, phenetyl, and 3-phenylpropyl. Examples of the halogeno aralkyl group have 7–9 carbon atoms and include halogenophenylmethyl, halogenophenylethyl, and halogenophenylpropyl. The halogen may be fluorine, chlorine, or bromine.

Preferred hydrocarbon groups $R^3$ and $R^4$ are alkyl groups having 1–5 carbon atoms (preferably 1–3 carbon atoms). Particularly preferred are methyl and ethyl. Methyl is most preferred.

Preferred examples of the aromatic aldehydes having the formula (2) include aldehydes of the phenyl-type (i.e., aromatic hydrocarbon group) comprising a benzene ring which may have one or more substituents and an aldehyde group directly attached to the benzene ring (e.g., benzaldehyde, 2,4,6-trimethylbenzaldehyde, and 2,4-dichlorobenzaldehyde) and aldehydes of the pyridine-type (which may be condensed with other aromatic ring) which may have one or more substituents and an aldehyde group directly attached to the pyridine ring (e.g., nicotinaldehyde, namely, pyridine-3-aldehyde).

Also preferred is 2,6-dimethyl-4-(4-fluorophenyl)-pyrimidine-5-carboaldehyde, which can be prepared in the manner as described in Japanese Patent Provisional Publication H1(1989)-261377. The details are as follows.

Ethyl acetoacetate and 4-fluorobenzaldehyde are caused to react in isopropanol in the presence of piperidine and acetic acid to give (E/Z)-3-ethoxycarbonyl-4-(4-fluorophenyl)-but-3-en-2-on. The obtained (E/Z)-3-ethoxycarbonyl- 4-(4-fluorophenyl)-but-3-en-2-on is then caused to react with acetoamidine hydrochloride in ethanol in the presence of sodium acetate to give ethyl 1,4-dihydro-2,6-dimethyl-4-(4-fluorophenyl)-pyrimidine-5-carboxylate. The obtained carboxylate is treated with chromium trioxide in acetic acid to give ethyl 2,6-dimethyl-4-(4-fluorophenyl) pyrimidine-5-carboxylate. The carboxylate is then treated with aluminum diisobutylhydride in toluene to produce 2,6-dimethyl-4-(4-fluorophenyl)-5-hydroxymethylpyrimidine. Finally, the obtained hydroxymethylpyrimidine is treated with pyridinium chlorochromate in dichloromethane to prepare the 2,6-dimethyl-4-(4-fluorophenyl)-pyrimidine-5-carboaldehyde.

Also preferred is 2,6-diisopropyl-4-(4'-fluorophenyl)-5-methoxymethyl-3-pyridinecarboxyaldehyde, which can be prepared in the manner as described in Japanese Patent Provisional Publication H1(1989)-216974. The details are as follows.

4-Fluorobenzaldehyde and ethyl isobutylyl acetate are caused to react in isopropanol in the presence of piperidine and acetic acid to give (E/Z)-4-ethoxycarbonyl-5-(4'-fluorophenyl)-2-methylpent-4-en-3-one. The obtained (E/Z)-4-ethoxycarbonyl-5-(4'-fluorophenyl)-2-methylpent-4-en-3-on is then caused to react with ethyl 3-amino-4-methyl pent-2-enoate in ethanol to give diethyl 1,4-dihydro-2,6-diisopropyl-4-(4'-fluorophenyl)-pyridine-3,5-dicarboxylate. The obtained dicarboxylate is caused to react with 2,3-dichloro-5,6-dicyano-p-benzoquinone in methylene chloride to give diethyl 2,6-diisopopyl-4-(4'-fluorophenyl)-pyridine-3,5-dicarboxylate. The dicarboxylate is then treated with sodium bis-(2-methoxyethoxy)-dihydroaluminate in dry tetrahydrofuran to produce ethyl 2,6-diisopropyl-4-(4'-fluorophenyl)-5-hydroxymethylpyridine-3-carboxylate. The obtained carboxylate is treated with methyl iodide and sodium hydride in dry tetrahydrofuran to give ethyl 2,6-diisopropyl-4-(4'-fluorophenyl)- 5-methoxymethyl-pyridine-3-carboxylate. The resulting carboxylate is treated with lithium aluminum hydride in dry tetrahydrofuran and then treated with aqueous potassium hydroxide to give 2,6-diisopropyl-4-(4'-fluorophenyl)-3-hydroxymethyl-5-methoxymethylpyridin. Finally, the obtained methoxymethyl-pyridine is treated with neutral alumina and pyridinium chlorochromate in methylene chloride to prepare the 2,6-diisopropyl-4-(41-fluorophenyl)-5-methoxymethyl-3-pyridinecarboxyaldehyde.

The oxyglutaric acid ester derivative of the formula (3) contains an asymmetric carbon atom, and therefore there are optical isomers. The process of the invention can be performed utilizing the oxyglutaric acid ester derivative in the form of any of racemate and optical isomers. The optical activity as well as the optical purity of the oxyglutaric acid ester are not varied in the process of the invention. Therefore, the 3-oxy-5-oxo-heptenoic acid derivative precisely corresponding to the starting oxyglutaric acid ester derivative in its optical activity and optical purity can be obtained.

The oxyglutaric acid ester derivative of the formula (3) preferably has an optical activity corresponding to R type of the absolute configuration. This oxyglutaric acid ester derivative can be prepared in the manner stated in Journal of Medicinal Chemistry, 1987, vol.30, No.10, pp.1858–1873. For instance, (R)-dimethyl {[3-[(tert-butyldimethylsilyl)oxy]-4-(methoxycarbonyl)butyryl]methyl}phosphonate can be prepared by the process comprising the following steps 1–7:

Step 1: Imidazole and tert-butylchlorodimethylsilane are added to a solution of diethyl 3-hydroxyglutarate in methylene chloride, and the reaction is performed to give diethyl 3-[(tert-butydimethylsilyl)-oxy]pentanedioate.

Step 2: To a solution of the obtained diethyl 3-[(tert-butydimethylsilyl)oxy]pentanedioete in methanol is added sodium hydroxide, and the reaction is performed to give a reaction mixture. Methanol is distilled off from the reaction mixture, and the residue is treated with benzene and acetic anhydride to give 3-[(tert-butyldimethylsilyl)oxy] pentanedioic acid anhydride.

Step 3: The acid anhydride obtained in Step 2, trimethylamine, (N,N-dimethylamino)pyridine, methylene chloride, and (R)-phenylethanol are caused to react to give a reaction mixture. The reaction mixture is post-treated, and is caused to react with diazomethane in diethyl ether to give (3R,1'R)-methyl-1'-phenylethyl-3-[(tert-butyldimethylsilyl)oxy]pentanedioate.

If (S)-phenylethanol is utilized in place of the (R)-phenylethanol in the above reaction, (3S,1'S)-methyl-1'-phenylethyl-3-[(tert-butyldimethylsilyl)oxy]pentanedioate is obtained. Alternatively, if phenylethanol (racemate) is utilized in place of the (R)-phenylethanol in the above reaction, methyl-1'-phenylethyl-3-[(tert-butyldimethylsilyl) oxy]pentanedioate is obtained. From each of the obtained products, 3-[(tert-butyldimethylsilyl)oxy]pentanedioate having the optical purity of the corresponding product is obtained by the steps set forth below.

Step 4: The (3R,1'R)-methyl-1'-phenylethyl-3-[(tert-butyldimethylsilyl)oxy]pentanedioate obtained in Step 3 is subjected to reaction by addition of a solution of hydrogen fluoride in acetonitrile to give (3R,1'R)-methyl-1'-phenylethyl-3-hydroxypentanedioate.

Step 5: To a reaction mixture of n-butyllithium and dimethyl methylphosphonate is added the (3R,1R)-methyl-1'-phenylethyl-3-hydroxypentanedioate obtained in Step 4, to give (R)-dimethyl [4-[(R)-phenylethoxycarbonyl]-3-hydroxybutyryl]methylphosphonate.

Step 6: The methylphosphonate obtained in Step 5 is caused to react with tert-butylchlorodimethylsilane in the presence of imidazole to give (R)-dimethyl [3-(tert-butyldimethylsilyloxy)-4-[(R)-phenylethoxycarbonyl] butyryl]methylphosphonate.

Step 7: The methylphosphonate obtained in Step 6 is caused to react with hydrogen in the presence of a palladium deposited on active carbon carrier to produce a reaction mixture. The reaction mixture is subjected to post-treatment, and further subjected to reaction with diazomethane in ether to give (R)-dimethyl [3-(tert-butyldimethylsilyloxy)-4-methoxycarbonylbutyryl]methylphosphonate, which is also called methyl (R)-3-tert-[(butyldimethylsilyl)oxy]-6-dimethoxyphosphinyl-5-oxohexanoate.

The oxyglutaric acid ester derivative of the formula (3) is generally employed in an amount of 0.5 to 2.0 moles, preferably 0.8 to 1.5 moles, most preferably 1.0 to 1.3 moles, per one mole of the aromatic aldehyde of the formula (2).

The reaction of the process of the invention is performed in an aliphatic alcohol containing a small amount of water in the presence of a base having the formula $M_xA$. "M" stands for an alkali metal such as lithium, sodium, potassium, rubidium, or cesium. Preferred are lithium, sodium, and potassium. "x" is 1 or 2, and 2 is preferred. "A" stands for a carbonic or hydrogen carbonic group, and the carbonic group is preferred. Accordingly, the base having the formula M is lithium carbonate, sodium carbonate, potassium carbonate, rubidium carbonate, cesium carbonate, sodium hydrogen carbonate, potassium hydrogen carbonate, or cesium hydrogen carbonate. Preferred are lithium carbonate, sodium carbonate, and potassium carbonate.

The base of the formula $M_xA$ is generally employed in an amount of 0.5 to 2.0 moles, preferably 0.7 to 1.8 moles, most preferably 0.8 to 1.5 moles, per one mole of the aromatic aldehyde of the formula (2).

The aliphatic alcohol employed as the solvent in the process of the invention preferably is an aliphatic alcohol having 1–10 carbon atoms (specifically 1–6 carbon atoms). Examples of the aliphatic alcohols include methyl alcohol (i.e., methanol), ethyl alcohol (i.e., ethanol), propyl alcohol, isopropyl alcohol, butanol, and isobutanol. Preferred aliphatic alcohols are propyl alcohol and isopropyl alcohol.

The alcohol employed as the reaction solvent in the process of the invention should contain water of 30 to 20,000 ppm, i.e., 0.003% to 2% by weight preferably 100 to 15,000 ppm. In the case of using ethanol, the content of water preferably is 200 to 20,000 ppm. In the case of using propanol (i.e., n-propanol), the content of water preferably is 3,000 to 20,000 ppm. In the case of using isopropanol, the content of water prerably is 1,000 to 20,000 ppm. The content of water more preferably less than 16,000 ppm, most preferably less than 15,000 ppm.

The aliphatic alcohol is generally used in an amount of 7.5 to 300 moles, preferably 10 to 100 moles, most preferably 15 to 80 moles, per one mole of the aromatic aldehyde.

If the aromatic aldehyde of the formula (2) and/or the oxyglutaric acid ester derivative of the formula (3) are not sufficiently soluble in the aliphatic alcohol, an organic solvent which can dissolve the aromatic aldehyde and/or the oryglutaric acid ester derivative therein can be employed in combination with the aliphatic alcohol as the reaction solvent. For instance, the aromatic aldehyde or oxyglutaric acid ester derivative is first dissolved in the non-alcoholic organic solvent to give an appropriate solution, and then aliphatic alcohol is added to the solution to give the solution for performing the desired reaction. The non-alcoholic organic solvent is selected from organic solvents which do not disturb the desired reaction. Examples of the non-alcoholic organic solvents include alicyclic ethers such as tetrahydrofuran, aliphatic ethers such as diethyl ether and diisopropyl ether, nitriles such as acetonitrile and propionitrile, halogenated hydrocarbons such as dichloromethane and chloroform, and non-protonic solvents such as dimethyl sulfoxide, dimethylformamide and 1,3-dimethyl-2-imidazoline. When the reaction solvent is a mixture of the aliphatic alcohol and other organic solvent, the aliphatic alcohol should be contained in the solvent in an amount of not less than 40 vol. %, preferably not less than 50 vol. %, more preferably not less than 80 vol. %.

The reaction of the process of the invention can be performed at a temperature of −30° to 50° C., preferably −25° to 40° C., most preferably −20° to 30° C. The reaction period generally ranges from 0.25 to 30 hours, preferably from 0.3 to 24 hours, most preferably 0.5 to 20 hours. The reaction can be performed in the presence of an atmospheric gas containing oxygen gas or under covering with an inert gas such as nitrogen gas.

After the reaction is complete, the desired product (i.e., the 3-oxy-5-oxo-6-heptenoic acid derivative) is recovered from the reaction mixture. The recovery can be performed utilizing the known techniques such as a washing procedure and a separating procedure. For instance, the reaction mixture is diluted with an organic solvent, washed with water to remove the inorganic base, extracted with an appropriate solvent, concentrated under reduced pressure, and subjected to column chromatography. The solvent employed for the dilution can be an aromatic hydrocarbon solvent such as benzene, toluene or xylene, an ester solvent such as ethyl acetate or propyl acetate, or a halogenated hydrocarbon solvent such as methylene chloride or chloroform.

The obtained 3-oxy-5-oxo-6-heptenoic acid derivative can be subjected to a step for removing the hydroxyl-protective group after the reaction mixture is washed with water.

As described hereinbefore, the obtained 3-oxy-5-oxo-6-heptenoic acid derivative can be in the form of a racemate or one of isomers (optical isomers or geometrical) depending upon the nature of one or both of the starting compounds, namely, the aromatic aldehyde of the formula (2) and the oxylutaric acid ester derivative of the formula (3). The racemate can be resolved to give the desired isomer by the known optical resolution method or separation method.

The 3-oxy-5-oxo-6-heptenoic acid derivative of the formula (1) obtained by the process of the invention can be converted into the 3-hydroxy-3-methylglutaryl Coenzyme A reductase preventive agent in the known method or a method analogous to the known method.

For instance, methyl (3R,6E)-3-[(tert-butyldimethylsilyl) oxy]-7-(2,4-dichlorophenyl)-5-oxo-6-heptenoate (which is one of the compounds of the formula (1)) is subjected to the tert-butyldimethylsilyl removing step using hydrogen fluoride in the manner as described in Japanese Patent Provisional Publication H5(1993)-178841, to give methyl (3R, 6E)-7-(2,4-dichlorophenyl)-3-hydroxy-5-oxo-6-heptenoate. The obtained ester is then subjected to Syn reduction using diethylmethoxyborane and sodium borohydride ($NaBH_4$), to give methyl (3R,5S,6E)-7-(2,4-dichlorophenyl)-3,5-dihydroxy-6-heptenoate. Subsequently, thus obtained ester is treated with sodium hydroxide and hydrochloric acid in the manner as described in Journal of Medicinal Chemistry, 1985, vol.28, No.3, pp.347–358, to give (+)-trans-(E)-6-[2-(2,4-dichlorophenyl)-ethenyl] 3,4,5,6-tetrahydro-4-hydroxy-2H-pyran-2-on which has the 3-hydroxy-3-methylglutaryl Coenzyme A reductase preventive action.

If the compound of the formula (1) is methyl (3R,6E)-3-[(tert-butyldimethylsilyl)oxy]-7-(2',6'-diisopropyl-4'-(4"-fluorophenyl)-5'- (methoxymethyl)pyridin-3'-yl]-5-oxo-6-heptenoate, it is subjected to the tert-butyldimethylsilyl removing step using hydrogen fluoride in the manner as described in Japanese Patent Provisional Publication H5(1993)-178841, to give methyl (3R,6E)-7-(2',6'-diisopropyl-4'-(4"-fluorophenyl)-5'-(methoxymethyl)-pyridin-3'-yl]-3-hydroxy-5-oxo-6-heptenoate. The obtained ester is then subjected to Syn reduction using diethylmethoxyborane and sodium borohydride ($NaBH_4$), to give methyl (3R,5S,6E)-7-(2',6'-diisopropyl-4'-(4"-fluorophenyl) -5-(methoxymethyl)pyridin-3'-yl]-3,5-dihydroxy-6-heptenoate. Subsequently thus obtained ester is treated with sodium hydroxide and hydrochloric acid in the manner as described in Japanese Patent Provisional Publication H3(1991)-501613 to give sodium (3R,5S,6E)-(+)-erythro-7-[2',6'-diisopropyl-4'- (4"-fluorophenyl)-5'-(methoxymethyl) pyridin-3'-yl]-3,5-dihydroxy-6-heptenoate, which has the 3-hydroxy-3-methylglutaryl Coenzyme A reductase preventive action.

The present invention is further described by the following non-limitative examples.

EXAMPLE 1

In 5 mL of isopropanol (water content:: 10,000 ppm) were dissolved 140 mg (1.3 mmol.) of nicotinaldehyde (pyridin-3-aldehyde) and 500 mg (1.3 mmol.) of methyl (R)-3-[(tert-butyldimethylsilyl)oxy]-6-(dimethoxyphosphinyl)-5-oxohexanoate (optical purity: 99% ee) to give an alcoholic solution. To the alcoholic solution was added 181 mg (1.3 mmol) of potassium carbonate, and the mixture was stirred for 3 hours at room temperature (22° C.). To the resulting reaction mixture was added 20 mL of ethyl acetate, and the mixture was stirred and washed with 10 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=1/1, volume ratio) to give 469 mg (yield: 99%) of methyl (3R, 6E)-3-[(tert-butyldimethylsilyl)oxy]-5-oxo-7-(pyridin-3-yl)-6-heptenoate.

$^1$H-NMR (CDCl$_3$, 400 MHz) δ: 0.05 (s, 1H), 0.08 (s, 1H), 0.83 (s, 9H), 2.54 (dd, 1H, J=14.7 and 5.9 Hz), 2.61 (dd, 1H, J=14.7 and 5.9 Hz), 2.91 (dd, 1H, J=15.6 and 5.4 Hz), 2.99 (dd, 1H, J=15.6 and 6.8 Hz), 3.69 (s, 3H), 4.68 (ddt, 1H, J=6.8, 5.9 and 5.4 Hz), 6.82 (d, 1H, J=16.6 Hz), 7.37 (dd, 1H, J=7.8 and 4.9 Hz), 7.55 (d, 1H, J=16.6 Hz), 7.89 (ddd, 1H, J=7.8, 2.0 and 1.5 Hz), 8.63 (dd, 1H, J=4.9 and 1.5 Hz), 8.78 (d, 1H, J=2.0 Hz).

EXAMPLE 2

The procedures of Example 1 were repeated except for employing isopropanol containing 50 ppm of water to give 401 mg (yield: 85%) of methyl (3R,6E)-3-[(tert-butyldimethylsilyl)oxy]-5-oxo-7-(pyridin-3-yl)-6-heptenoate.

EXAMPLE 3

The procedures of Example 1 were repeated except for employing 139 mg (1.3 mmol.) of benzaldehyde in place of the nicotinaldehyde to give 450 mg (yield: 95%) of methyl (3R,6E)-3-[(tert-butyldimethylsilyl)oxy]-5-oxo-7-phenyl-6-heptenoate.

$^1$H-NMR (CDCl$_3$, 400 MHz) δ: 0.04 (s, 1H), 0.08 (s, 1H), 0.84 (s, 9H), 2.53 (dd, 1H, J=14.7 and 6.4 Hz), 2.61 (dd, 1H, J=14.7 and 5.9 Hz), 2.88 (dd, 1H, J=15.6 and 5.9 Hz), 2.98 (dd, 1H, J=15.6 and 6.4 Hz), 3.68 (s, 3H), 4.68 (tt, 1H, J=6.4 and 5.9 Hz), 6.75 (d, 1H, J=16.1 Hz), 7.38–7.42 (m, 3H), 7.52–7.60 (m, 2H), 7.56 (d, 1H, J=16.1 Hz).

The optical purity of the obtained methyl (3R,6E)-3-[(tert-butyldimethylsilyl)oxy]-5-oxo-7-phenyl-6-heptenoate was measured under the following conditions to give the optical purity of 99% ee.

Conditions for measurement of optical purity

Column: CHIRALCEL OD

Eluent: hexane/ethanol/trifluoroacetic acid=100/0.5/0.01 (volume ratio)

Flow rate: 1.0 mL/min.

Detector: UV (wavelength: 260 nm)

Temperature: 30° C.

Concentration of Sample: 10 mg/10 mL (eluent)

EXAMPLE 4

The procedures of Example 3 were repeated except for employing, as the reaction solvent, methanol containing 120 ppm of water to give 422 mg (yield: 89%) of methyl (3R,6E)-3-[(tert-butyldimethylsilyl)oxy]-5-oxo-7-phenyl-6-heptenoate.

EXAMPLE 5

The procedures of Example 3 were repeated except for employing 194 mg (1.3 mmol.) of 2,4,6-trimethylbenzaldehyde in place of the nicotinaldehyde to give 423 mg (yield: 80%) of methyl (3R,6E)-3-[(tert-butyldimethylsilyl)oxy]-5-oxo-7-phenyl-6-heptenoate.

$^1$H-NMR (CDCl$_3$, 400 MHz) δ: 0.06 (s, 1H), 0.08 (s, 1H), 0.84 (s, 9H), 2.29 (s, 3H), 2.33 (s, 6H), 2.54 (dd, 1H, J=14.7 and 6.4 Hz), 2.62 (dd, 1H, J=14.7 and 5.9 Hz), 2.86 (dd, 1H, J=15.6 and 5.9 Hz), 2.96 (dd, 1H, J=15.6 and 6.9 Hz), 3.68 (s, 3H), 4.71 (ddt, 1H, J=6.9, 6.4 and 5.9 Hz), 6.36 (d, 1H, J=6.6 Hz), 6.90 (s, 3H), 7.73 (d, 1H, J=16.6 Hz).

The optical purity of the obtained methyl (3R,6E)-3-[(tert-butyldimethylsilyl)oxy]-5-oxo-7-(2,4,6-trimethylphenyl)-6-heptenoate was measured under the following conditions to give the optical purity of 99% ee.

Conditions for measurement of optical purity

Column: CHIRALCEL OD

Eluent: hexane/ethanol/trifluoroacetic acid=100/0.5/0.01 (volume ratio)

Flow rate: 0.7 mL/min.

Detector: UV (wavelength: 260 nm)

Temperature: 30° C.

Concentration of Sample: 10 mg/10 mL (eluent)

EXAMPLE 6

In 10 mL of isopropanol (water content: 9,500 ppm) were dissolved 457 mg (2.6 mmol.) of 2,4-dichlorobenzaldehyde and 1.0 g (2.6 mmol.) of methyl 3-[(tert-butyldimethylsilyl)oxy]-6-(dimethoxyphosphinyl)-5-oxohexanoate to give an alcoholic solution. To the alcoholic solution was added 362 mg (2.3 mmol) of potassium carbonate, and the mixture was stirred for 3 hours at room temperature (22° C.). To the resulting reaction mixture was added 40 mL of ethyl acetate, and the mixture was stirred and washed with 20 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=95/5, volume ratio) to give 1.06 g (yield: 94%) of methyl (E)-3-[(tert-butyldimethylsilyl)oxy]-7-(2,4-dichlorophenyl)-5-oxo-6-heptenoate.

$^1$H-NMR (CDCl$_3$, 400 MHz) δ: 0.05 (s, 3H), 0.08 (s, 3H), 0.83 (s, 3H), 2.54 (dd, 1H, J=14.7 and 6.4 Hz), 2.61 (dd, 1H, J=14.7 and 5.9 Hz), 2.90 (dd, 1H, J=15.6 and 5.9 Hz), 3.00 (dd, 1H, J=:15.6 and 6.4 Hz), 3.68 (s, 3H), 4.67 (tt, 1H, J=E;.4 and 5.9 Hz), 6.68 (d, 1H, J=16.1 Hz), 7.28 (dd, 1H, J=8.3 and 2.0 Hz), 7.46 (d, 1H, J=2.0 Hz), 7.56 (d, 1H, J=8.3 Hz), 7.88 (d, 1H, J=16.1 Hz).

EXAMPLE 7

In 5 mL of ethanol (water content: 11,800 ppm) were dissolved 427 mg (1.3 mmol.) of 2,6-diisopropyl-4-(4'-fluorophenyl)-5-methoxymethyl-3-pyridinecarboxyaldehyde and 550 mg (1.43 mmol.) of methyl (R)-3-[(tert-butyldimethylsilyl)oxy]-6-(dimethoxyphosphinyl)-1,-oxohexanoate (optical purity: 99% ee) to give an ethanolic solution. To the ethanolic solution was added 199 mg (1.43 mmol) of potassium carbonate, and the mixture was stirred for 8 hours at room temperature (20° C.). To the resulting reaction mixture was added 20 mL of ethyl acetate, and the mixture was stirred and washed with 10 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=95/5, volume ratio) to give 639 mg (yield: 84%) of methyl (3R,6E)-3-[(tert-butyldimethylsilyl)oxy]-7[2',6'-diisopropyl-4'(4'-fluorophenyl)-5'-(methoxymethyl)pyridin-3'-yl]-5-oxo-6-heptenoate.

$^1$H-NMR (CDCl$_3$, 400 MHz) δ: −0.02 (s, 3H), 0.03 (s, 3H), 0.81 (s, 9H), 1.26 (d, 3H, J=6.8 Hz), 1.27 (d, 3H, J=6.8

Hz), 1.33 (d, 6H, J=5.9 Hz), 2.39 (dd, 1H, J=14.7 and 6.94 Hz), 2.45 (dd, 1H, J=14.7 and 5.4 Hz), 2.57 (dd, 1H, J=15.6 and 5.9 Hz)., 2.62 (dd, 1H, J=6.8 and 6.4 Hz), 3.20 (3S, 3H), 2.28 (qq, 1H, J=6.8 and 6.4 Hz), 3.38 (qq, 1H, J=6.8 and 6.4 Hz), 3.66 (s, 3H), 4.60 (s, 2H), 4.52 (tt, 1H, J=6.4 and 5.9 Hz), 5.89 (d, 1H, J=16.6 Hz), 7.06–7.18 (m, 4H), 7.34 (d, 1H, J=16.6 Hz).

Elemental Analysis:

Calc. for $C_{33}H_{48}NO_5FSi$: C 67.66%, H 8.25%, N 2.39% Found: C 67.71%, H 8.27%, N 2.45%. IR (KBr) $cm^{-1}$: 777, 842, 1100, 1509, 1667, 1740 $[\alpha]_D^{25}$: −11.4° (c=1.00, chloroform) m.p. : 61.5°–63.50° C.

The optical purity of the obtained methyl (3R,6E)-3-[(tert-butyldimethylsilyl)oxy]-7[2',6'-diisopropyl-4'(4"-fluorophenyl)-5'-(methoxymethyl)pyridin -3'-yl]-5-oxo-6-heptenoate was measured under the following conditions to give the optical purity of 99% ee.

Conditions for measurement of optical purity

Column: CHIRALCEL OD

Eluent: hexane/ethanol/trifluoroacetic acid=100/0.3/0.01 (volume ratio)

Flow rate: 0.4 mL/min.

Detector: UV (wavelength: 260 nm)

Temperature: 30° C.

Concentration of Sample: 5 mg/10 mL (eluent)

EXAMPLE 8

In 5 mL of isopropanol (water content: 6,000 ppm) were dissolved 427 mg (1.3 mmol.) of 2,6-diisopropyl-4-(4'-fluorophenyl)-5-methoxymethyl-3-pyridinecarboxyaldehyde and 550 mg (1.43 mmol.) of methyl (R)-3-[(tert-butyldimethylsilyl)oxy]-6-(dimethoxyphosphinyl)-5-oxohexanoate (optical purity: 99% ee) to give an isopropanolic solution. To the isopropanolic solution was added 199 mg (1.43 mmol) of potassium carbonate, and the mixture was stirred for 8 hours at room temperature (22° C.). To the resulting reaction mixture was added 20 mL of ethyl acetate, and the mixture was stirred and washed with 10 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=95/5, volume ratio) to give 675 mg (yield: 88%) of methyl (3R,6E)-3-[(tert-butyldimethylsilyl)oxy]-7[2',6'-diisopropyl-4'(4'-fluorophenyl)-5'-(methoxymethyl)pyridin -3'-yl)-5-oxo-6-heptenoate.

EXAMPLE 9

In 5 mL of isopropanol (water content: 3,000 ppm) were dissolved 427 mg (1.3 mmol.) of 2,6-diisopropyl-4-(4'-fluorophenyl)-5-methoxymethyl-3-pyridinecarboxyaldehyde and 550 mg (1.43 mmol.) of methyl (R)-3-[(tert-butyldimethylsilyl)oxy]-6-(dimethoxyphosphinyl)-5-oxohexanoate (optical purity: 99% ee) to give an isopropanolic solution. To the isopropanolic solution was added 199 mg (1.43 mmol) of potassium carbonate, and the mixture was stirred for 8 hours at room temperature (22° C.). To the resulting reaction mixture was added 20 mL of ethyl acetate, and the mixture was stirred and washed with 10 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=95/5, volume ratio) to give 613 mg (yield: 80%) of methyl (3R,6E)-3-((tert-butyldimethylsilyl)oxy]-7[2',6'-diisopropyl-4'(4"-fluorophenyl)-5'- (methoxymethyl)pyridin -3'-yl]-5-oxo-6-heptenoate.

COMPARISON EXAMPLE 1

In 3 mL of acetonitrile were dissolved 427 mg (1.3 mmol.) of 2,6-diisopropyl-4-(4'-fluorophenyl)-5-methoxymethyl-3-pyridinecarboxyaldehyde and 550 mg (1.43 mmol.) of methyl (R)-3-[(tert-butyldimethylsilyl)oxy] -6-(dimethoxyphosphinyl)- 5-oxohexanoate (optical purity: 99% ee) to give an acetonitrile solution. To the acetonitrile solution was added a solution of 61.5 mg (1.43 mmol.) of lithium chloride and 201 mg (1.32 mmol.) of DBU in 2.2 mL of acetonitrile, and the mixture was stirred for 25 hours at room temperature (20° C.). To the resulting reaction mixture was added 20 mL of ethyl acetate, and the mixture was stirred and washed with 10 mL of water. The washing was repeated twice. The organic phase was separated, dried over anhydrous magnesium sulfate, and filtered to give a filtrate. The filtrate was concentrated under reduced pressure, and the residue was subjected to silica gel column chromatography (eluent: hexane/ethyl acetate=95/5, volume ratio) to give 105 mg (yield: 14%) of methyl (3R,6E)-3-[(tert-butyldimethylsilyl)oxy]-7[2',6'-diisopropyl-4'(4"-fluorophenyl)-5'-(methoxymethyl)pyridin-3'-yl]-5-oxo-6-heptenoate.

We claim:

1. Methyl (3R,6E)-3-[(tert-butyldimethylsilyl)-oxy]-7-[2', 6'-diisopropyl-4'-(4"-fluorophenyl)-5'-(methoxymethyl) pyridin-3'-yl]-5-oxo-6-heptenoate.

2. A process for the preparation of methyl (3R,6E)-3-[(tert-butyldimethylsilyl)oxy]-7-[2',6'-diisopropyl-4'-(4"-fluorophenyl)-5'-(methoxymethyl)pyridin-3'-yl]-5-oxo-6-heptanoate which comprises reacting 2,6-diisopropyl-4-(4'-fluorophenyl)-5-methoxymethyl-3-pyridincarboxyaldehyde with methyl (R)-3-tert-[(butyldimehtylsilyl)oxy]-6-(dimethoxyphosphinyl)-5-oxohexanoate in an aliphatic alcohol having I to 10 carbon atoms in the presence of potassium carbonate.

3. The process of claim 2, wherein the aliphatic alcohol contains 30 to 20,000 ppm of water.

4. The process of claim 2, wherein the aliphatic alcohol contains 100 to 20,000 ppm of water.

* * * * *